Nov. 28, 1939. R. L. BYRUM Plant Pat. 348
ROSE
Filed May 10, 1939
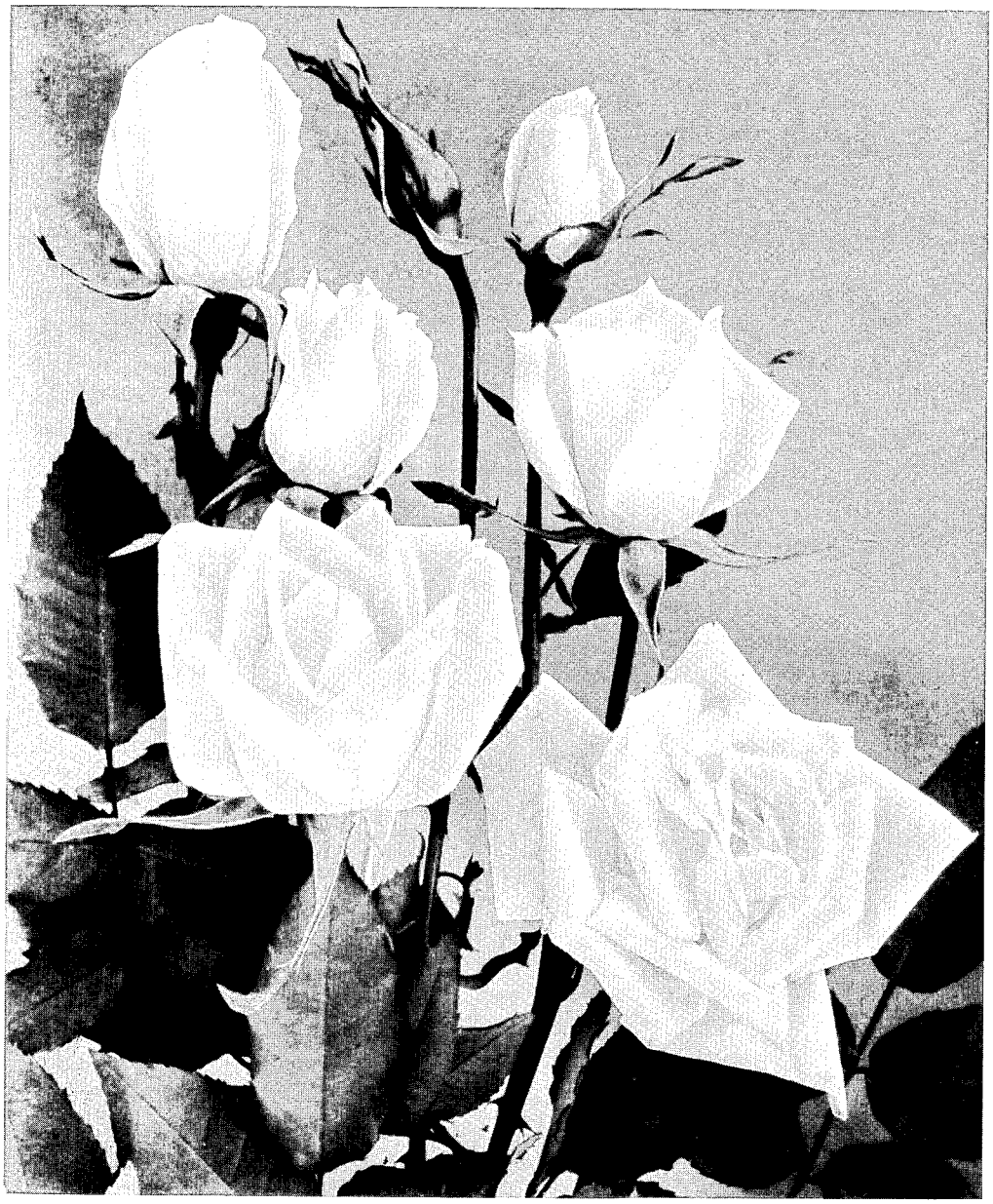
Inventor
Roy L. Byrum
By Robert Robb
Attorneys Patented Nov. 28, 1939

Plant Pat. 348

UNITED STATES PATENT OFFICE

348

ROSE

Roy L. Byrum, Richmond, Ind., assignor to Joseph H. Hill Company, Richmond, Ind.

Application May 10, 1939, Serial No. 272,885

1 Claim. (Cl. 47—61)

The present invention relates to a new and distinct variety of Hybrid Tea rose plant, the result of a definite effort to improve upon the known variety "White Briarcliff". The last-named rose is of no value as a greenhouse forcing variety because it lacks proper petal texture, produces weak stems, and has other unfavorable qualities.

In an attempt to improve these undesirable characteristics "Joanna Hill", which possesses qualities desirable in a white rose was used as the seed parent in crossing these two varieties, thus producing the successful result in the new variety herein set forth.

Enumerating the improved features, this new variety is found to be a stronger grower, has better petal texture, better bud form, larger flowers, stronger stems and larger foliage than White Briarcliff. It is also far superior to any white rose for forcing purposes.

Asexual reproduction shows the distinguishing characteristics hold through succeeding propagations by cuttings, grafting and budding.

The following is a detail description of the new variety, using general dictionary color terms excepting where otherwise indicated:

Parentage:
- Seedling—
  - *Seed parent.*—Joanna Hill.
  - *Pollen parent.*—White Briarcliff.

Classification:
- *Botanic and commercial.*—Hybrid Tea.

*Flower*

Blooming habit:
- Observations made in greenhouses of the Joseph H. Hill Company, Richmond, Indiana, during the month of March, 1939.
- Recurrent—continuous.

Bud:
- Before calyx breaks—
  - *Size.*—Large.
  - *Form.*—Long, pointed, with a conspicuous neck; with foliaceous appendages on the surface of the bud; with much cut foliaceour parts extending beyond the tip of the bud equal to more than its length.
  - *Color.*—Light Green Yellow (Ridgway's Plate 5).
- As first petal opens—
  - *Size.*—Large.
  - *Form.*—Long, pointed.
  - *Color.*—Outside—Light Green Yellow (Ridgway's Plate 5) at base, balance white. Inside—Light Green Yellow (Ridgway's Plate 5) at base, balance white.
  - *Peduncle.* — Length — medium; medium heavy. Strength—erect, stiff. Color—medium green. Aspect—entirely smooth.
  - *Opening.*—Opens up well.

Bloom:
- *Size.*—Large.
- *Average size when fully expanded.*—Five inches.
- *Borne.*—Singly, on strong, long stems.
- *Form.*—High center; petals remaining at first very loosely rolled outward remaining so at maturity.
- *Petalage.*—Double; 30 to 40 petals, arranged regularly.

Petals:
- *Texture.*—Thick, with inside and outside satiny.
- *Shape.*—Outside—obovate with apex rounded. Intermediate—obovate with apex more pointed. Inside—obovate with apex pointed.
- *Color.*—White (Ridgway's plate 53). Outside petal: outside surface—White (Ridgway's Plate 53); inside surface—Base Light Green Yellow (Ridgway's Plate 5). Intermediate petal and inner petal: outside and inside surface—White, base Light Green Yellow (Ridgway's Plate 5).
- *Persistence.*—Persist.
- *Fragrance.*—Moderate. Nature—Tea.
- *Lasting quality.*—As cut flowers grown in greenhouse kept at living room temperature—seven days.

Genital organs:
- *Stamens.*—Many arranged irregularly about pistils.
- *Filaments.*—Short, many with anthers. Color—White.
- *Anthers.*—Medium length, all open at once. Color—Yellow.
- *Pollen.*—Moderate; lemon color.
- *Pistils.*—Many.
- *Styles.*—Uneven, short, thin, bunched.
- *Stigmas.*—White.
- *Ovaries.*—All enclosed in calyx.
- *Hips.*—Long, pointed with inconspicuous neck; green; smooth; walls thin. Sepals—permanent; long; curled. Seeds—many; medium size.

*Plant*

Form:
- Bush.

Growth:
- Bushy, much branched, vigorous. Canes, heavy; main stems—green.

Foliage:

*Leaves.*—Very abundant, large, leathery.

*Leaflets.*—Five. Shape—ovoid with apex acute; base obtuse; margin simply irregularly serrate.

*Color.*—New foliage: upper side—Green—Bronze—Red; under side—Green—Bronze—Red. Old foliage: upper side—Dark Green; under side—Light Green.

*Rachis.*—Heavy. Upper side—grooved, hairy; under side—sparsely, thorny.

*Stipules.*—Long, wide, long points turning out at an angle of less than 45°.

*Disease resistance.*—Resistant to mildew and blackspot.

Thorns (divided into thorns, prickles and short needles):

*Thorns.*—Quantity—several. Form—medium length, hooked downward with long narrow base.

*Prickles.*—None.

*Hairs.*—None.

*Branches.*—Dull green. Thorns—several; form—medium length, hooked downward with long narrow base. Prickles—none. Hairs—none.

*New shoots.*—Color—Dull Bronze. Thorns—several; form—short length, straight with narrow base. Prickles—none. Hairs—none.

I claim:

A new and distinct variety of White Hybrid Tea rose characterized as to novelty by its vigorous growth, good petal texture, bud form, large flowers, strong stems, large foliage, and superior quality for forcing, substantially as shown and described.

ROY L. BYRUM.